(12) United States Patent
Tsubuku

(10) Patent No.: US 10,045,815 B2
(45) Date of Patent: Aug. 14, 2018

(54) ENERGY TREATMENT DEVICE AND ENERGY CONTROL DEVICE

(71) Applicant: OLYMPUS CORPORATION, Hachioji-shi, Tokyo (JP)

(72) Inventor: Yoshihiro Tsubuku, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/788,069

(22) Filed: Oct. 19, 2017

(65) Prior Publication Data

US 2018/0036066 A1    Feb. 8, 2018

Related U.S. Application Data

(63) Continuation of application No. PCT/JP2016/062129, filed on Apr. 15, 2016.

(30) Foreign Application Priority Data

May 7, 2015    (JP) .................................. 2015-094910

(51) Int. Cl.
| | |
|---|---|
| *A61B 18/14* | (2006.01) |
| *A61N 7/02* | (2006.01) |
| *A61B 17/32* | (2006.01) |
| *A61B 18/00* | (2006.01) |

(52) U.S. Cl.
CPC .. *A61B 18/1445* (2013.01); *A61B 17/320068* (2013.01); *A61N 7/02* (2013.01);
(Continued)

(58) Field of Classification Search
CPC .. A61B 2018/0019; A61B 2018/00994; A61B 2018/00642; A61B 2018/00755;
(Continued)

(56) References Cited

U.S. PATENT DOCUMENTS

| | | |
|---|---|---|
| 5,540,684 A | 7/1996 | Hassler, Jr. |
| 2009/0254080 A1 | 10/2009 | Honda |

(Continued)

FOREIGN PATENT DOCUMENTS

| | | |
|---|---|---|
| JP | 2009-247887 A | 10/2009 |
| JP | 2011-125714 A | 6/2011 |

(Continued)

OTHER PUBLICATIONS

Jul. 12, 2016 International Search Report issued in Patent Application No. PCT/JP2016/062129.

(Continued)

*Primary Examiner* — Joseph Stoklosa
*Assistant Examiner* — Sean W Collins
(74) *Attorney, Agent, or Firm* — Oliff PLC

(57) ABSTRACT

A switch detector of an energy treatment device detects a switch from a gradually decreasing state to a gradually increasing state on the basis of a detection result of acoustic impedance. In a state where ultrasonic electric energy and high-frequency electric energy are simultaneously output from an energy source, a controller stops an output of the ultrasonic electric energy on the basis of a fact that the switch of the acoustic impedance from the gradually decreasing state to the gradually increasing state is detected, and stops an output of the high-frequency electric energy on the basis of the fact that high-frequency impedance reaches a set threshold.

4 Claims, 8 Drawing Sheets

(52) U.S. Cl.
CPC ............ *A61B 17/320092* (2013.01); *A61B 2018/00642* (2013.01); *A61B 2018/00755* (2013.01); *A61B 2018/00875* (2013.01); *A61B 2018/00994* (2013.01)

(58) Field of Classification Search
CPC .. A61B 2018/00875; A61B 17/320092; A61B 2017/00017; A61B 2017/00145; A61B 18/1445; A61N 7/02
USPC ............ 606/50, 51, 52, 169, 205, 207
See application file for complete search history.

(56) References Cited

U.S. PATENT DOCUMENTS

2009/0259221 A1* 10/2009 Tahara ............ A61B 17/320092 606/34
2009/0326569 A1* 12/2009 Tanaka ............ A61B 17/320068 606/169
2011/0015627 A1 1/2011 DiNardo et al.
2011/0144635 A1 6/2011 Harper et al.
2013/0066238 A1 3/2013 Irisawa et al.

FOREIGN PATENT DOCUMENTS

JP 2012-533346 A 12/2012
WO 2012/108295 A1 8/2012

OTHER PUBLICATIONS

Jan. 10, 2017 Office Action issued in Japanese Patent Application No. 2016-561878.

\* cited by examiner

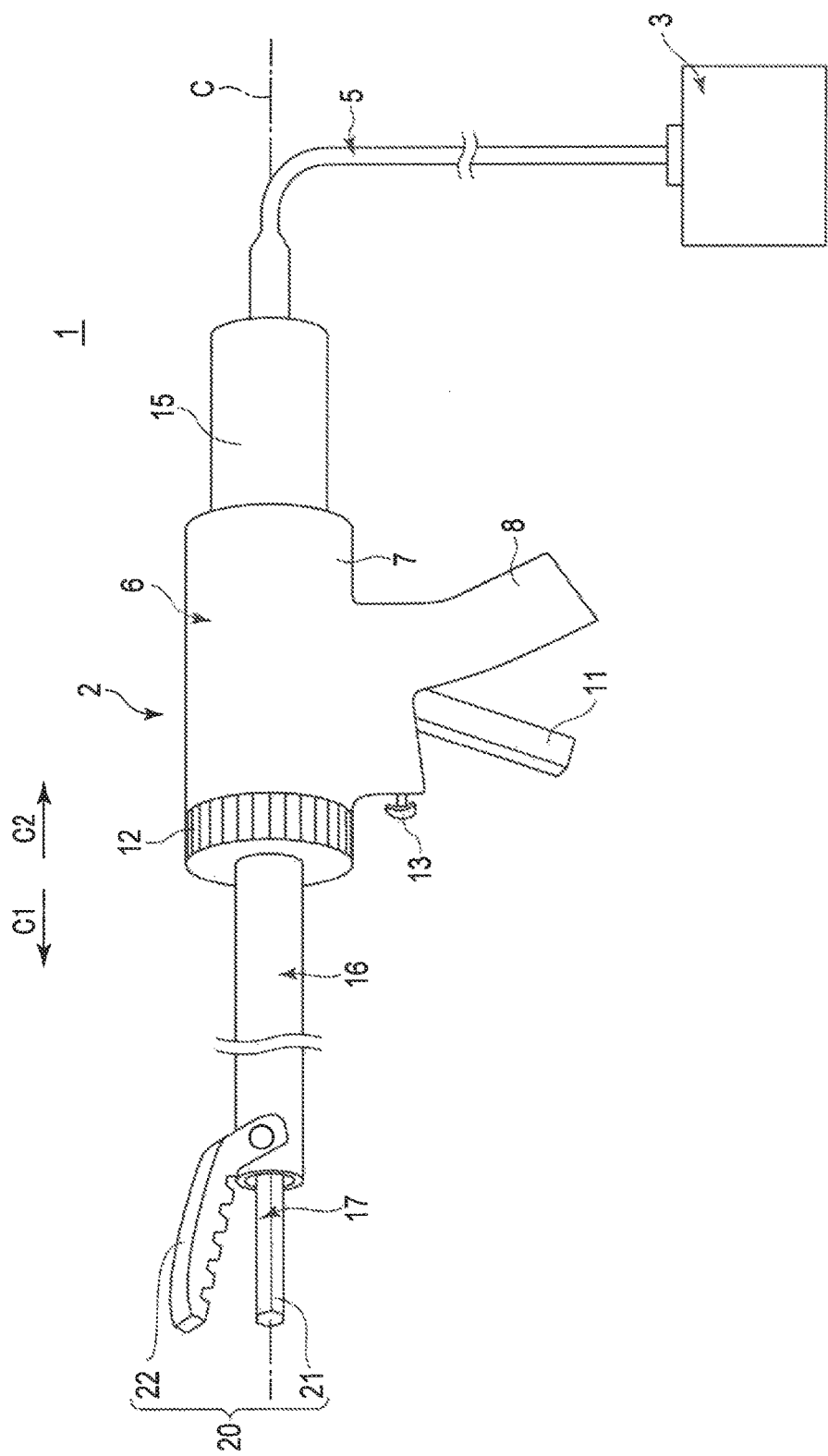
F I G. 1

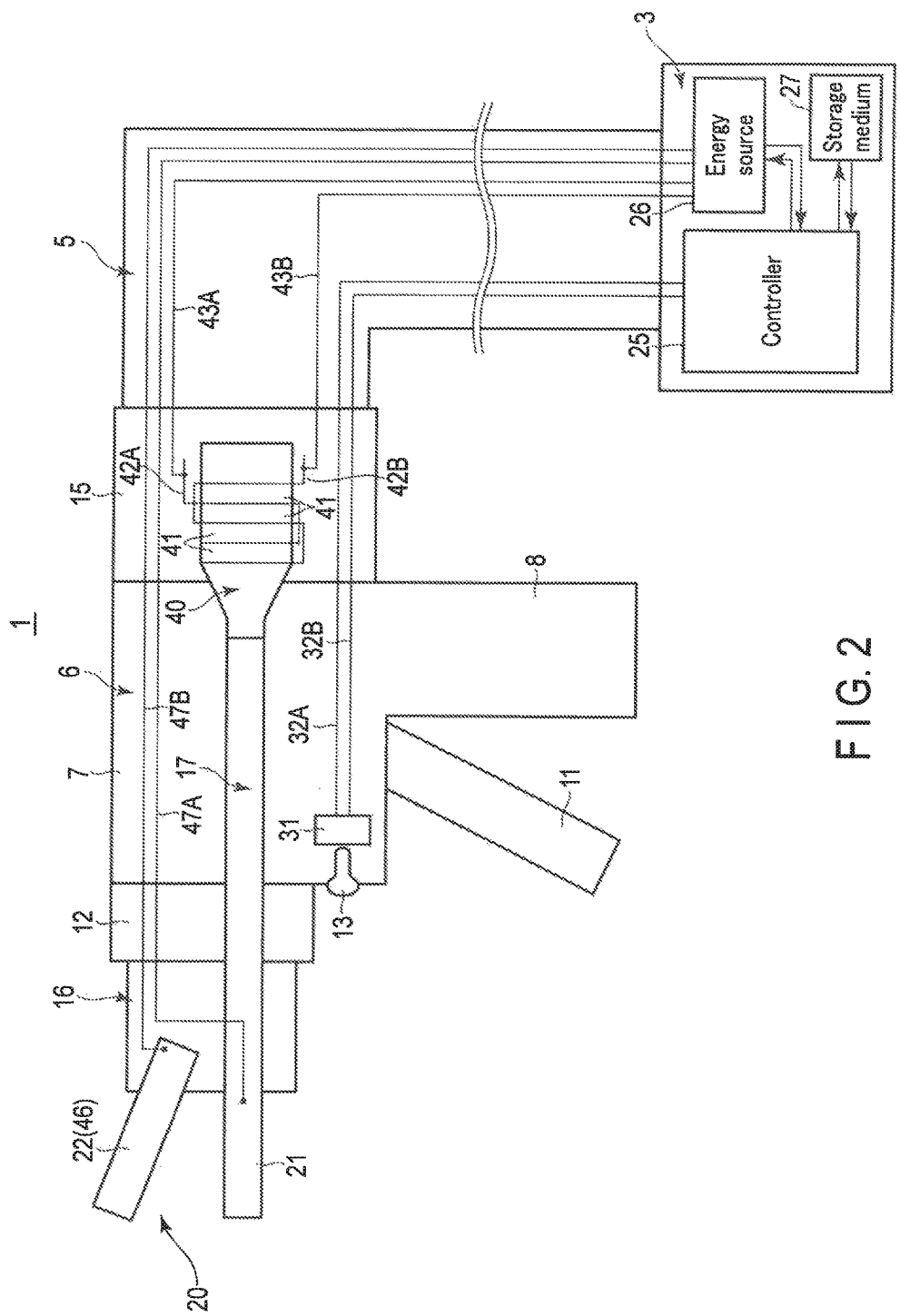
F I G. 2

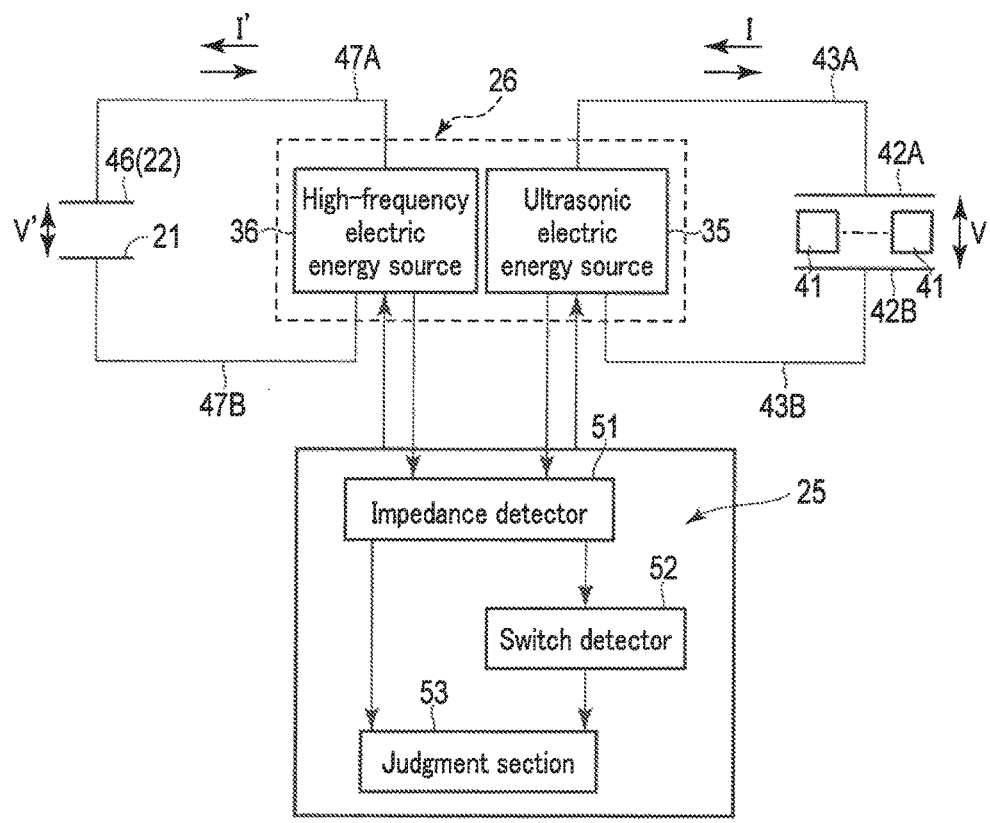
F I G. 3
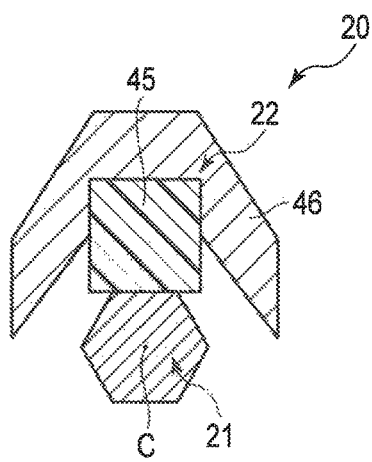
F I G. 4

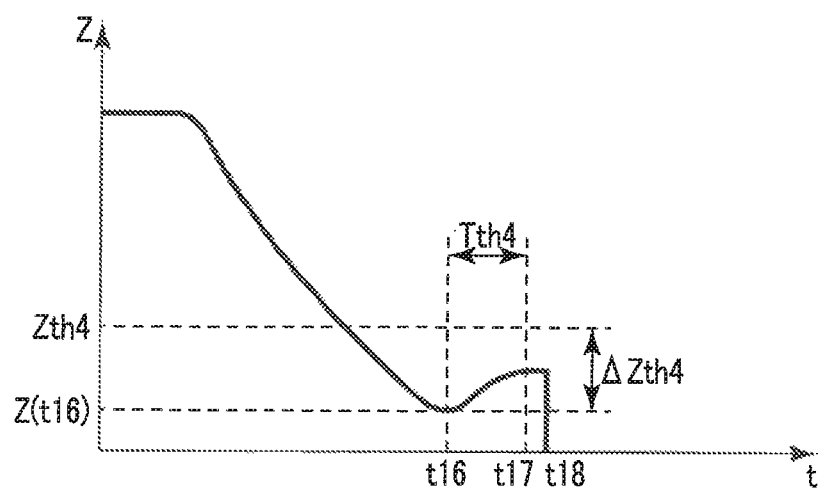
F I G. 10

ENERGY TREATMENT DEVICE AND ENERGY CONTROL DEVICE

CROSS-REFERENCE TO RELATED APPLICATIONS

This is a Continuation Application of PCT Application No. PCT/JP2016/062129, filed Apr. 15, 2016 and based upon and claiming the benefit of priority from prior Japanese Patent Application No. 2015-094910, filed May 7, 2015, the entire contents of which are incorporated herein by reference.

BACKGROUND OF THE INVENTION

1. Field of the Invention

The present invention relates to an energy treatment device and an energy control device which simultaneously use ultrasonic vibration and high-frequency electric energy to conduct a treatment.

2. Description of the Related Art

The specification of U.S. Pat. No. 5,540,684 discloses an energy treatment device in which an end effector performs coagulation or the like of a treated target by use of supplied high-frequency electric energy to treat the treated target. This energy treatment device detects high-frequency impedance (tissue impedance) with time when the supply of the high-frequency electric energy is started. The output of the high-frequency electric energy to the end effector is stopped on the basis of a rise of the high-frequency impedance to a set threshold. This prevents the carbonization of the treated target which is coagulated, and also prevents the adhering of the treated target (living tissue) to electrodes.

BRIEF SUMMARY OF THE INVENTION

According to one aspect of the invention, an energy treatment device including: an energy source which can output ultrasonic electric energy and high-frequency electric energy; a vibration generator which is supplied with the ultrasonic electric energy from the energy source, and thereby which is configured to generate ultrasonic vibration; an end effector configured to conduct a treatment by use of the ultrasonic vibration generated in the vibration generator and the high-frequency electric energy supplied from the energy source; an impedance detector which is configured to detect acoustic impedance with time in a state where the ultrasonic electric energy is output from the energy source, and which is configured to detect high-frequency impedance with time in a state where the high-frequency electric energy is output from the energy source; a switch detector which is configured to detect a switch from a gradually decreasing state where the acoustic impedance gradually decreases with time to a gradually increasing state where the acoustic impedance gradually increases with time, on the basis of the detection result of the acoustic impedance in the impedance detector; and a controller which is configured to control the output state of the ultrasonic electric energy and the output state of the high-frequency electric energy from the energy source, wherein in a state where the ultrasonic electric energy and the high-frequency electric energy are simultaneously output from the energy source, the controller is configured to stop the output of the ultrasonic electric energy on the basis of the fact that the switch of the acoustic impedance from the gradually decreasing state to the gradually increasing state is detected by the switch detector, and the controller is configured to stop the output of the high-frequency electric energy on the basis of the fact that the high-frequency impedance detected by the impedance detector reaches a set threshold.

According to one another aspect of the invention, an energy control device which controls the supply of energy to an energy treatment instrument, the energy treatment instrument including an end effector configured to conduct a treatment by use of ultrasonic vibration and high-frequency electric energy, and a vibration generator which is supplied with ultrasonic electric energy and thereby configured to generate the ultrasonic vibration to be transmitted to the end effector, the energy control device including: an energy source which can output the ultrasonic electric energy to be supplied to the vibration generator and the high-frequency electric energy to be supplied to the end effector; an impedance detector which is configured to detect acoustic impedance with time in a state where the ultrasonic electric energy is output from the energy source, and which is configured to detect high-frequency impedance with time in a state where the high-frequency electric energy is output from the energy source; a switch detector which is configured to detect a switch from a gradually decreasing state where the acoustic impedance gradually decreases with time to a gradually increasing state where the acoustic impedance gradually increases with time, on the basis of the detection result of the acoustic impedance in the impedance detector; and a controller which is configured to control the output state of the ultrasonic electric energy and the output state of the high-frequency electric energy from the energy source, wherein in a state where the ultrasonic electric energy and the high-frequency electric energy are simultaneously output from the energy source, the controller is configured to stop the output of the ultrasonic electric energy on the basis of the fact that the switch of the acoustic impedance from the gradually decreasing state to the gradually increasing state is detected by the switch detector, and the controller is configured to stop the output of the high-frequency electric energy on the basis of the fact that the high-frequency impedance detected by the impedance detector reaches a set threshold.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram showing an energy treatment device according to a first embodiment;

FIG. 2 is a schematic diagram showing an electric connection state between an energy treatment instrument and an energy control device, and a configuration to supply energy to an end effector, according to the first embodiment;

FIG. 3 is a schematic diagram showing a configuration to control the output of energy from an energy source according to the first embodiment;

FIG. 4 is a sectional view schematically showing the end effector according to the first embodiment through a section perpendicular to a longitudinal axis;

FIG. 10 is a schematic diagram showing an example different from those in FIG. 6 and FIG. 8 of a change of the acoustic impedance with time after the outputs of ultrasonic electric energy and high-frequency electric energy are simultaneously started.

Figure 5:
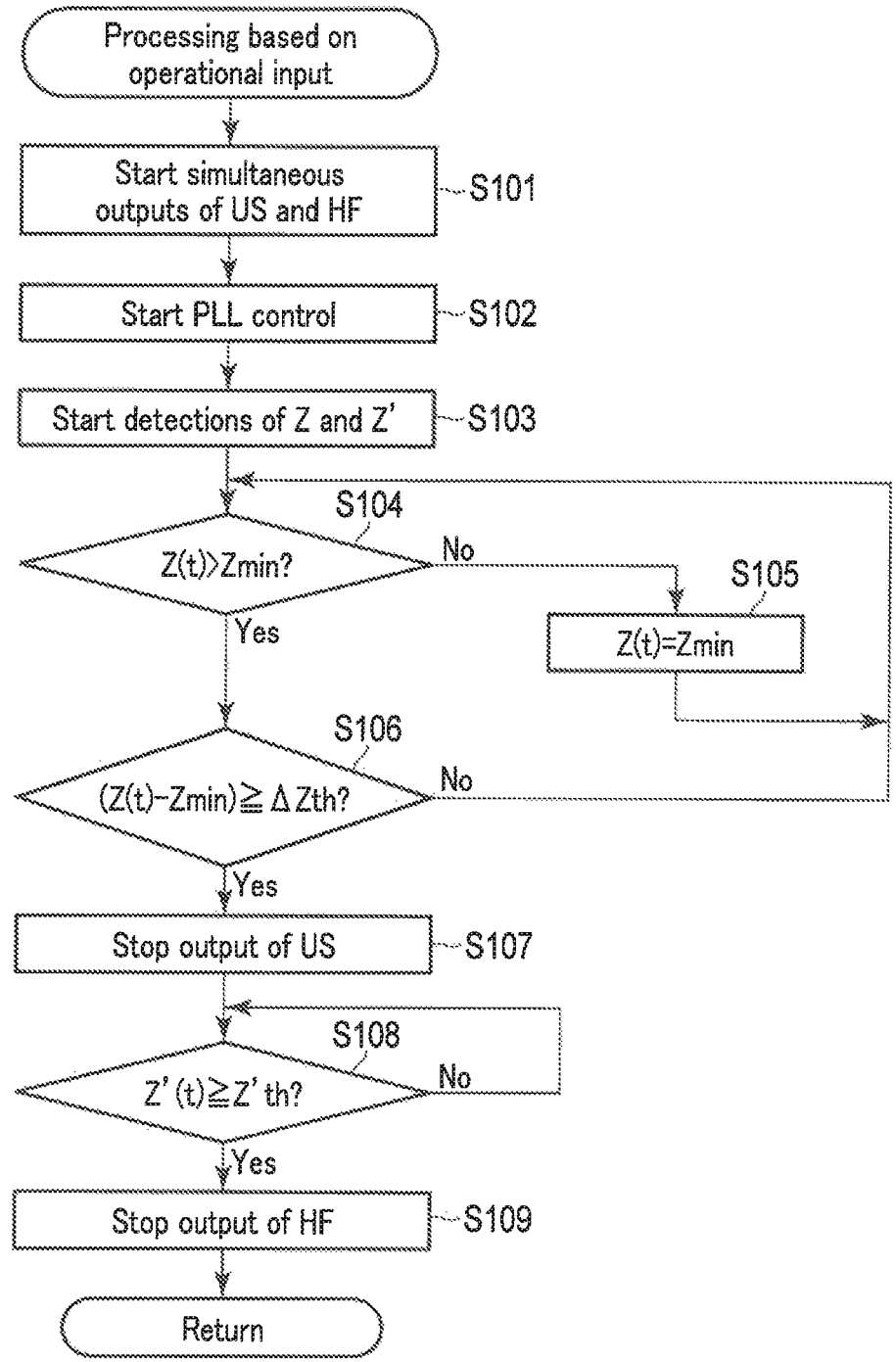
FIG. 5 is a flowchart showing processing in the energy control device based on an operational input in an operational button according to the first embodiment.

DETAILED DESCRIPTION OF THE INVENTION (First Embodiment)

A first embodiment of the present invention is described with reference to FIG. 1 to FIG. 8. FIG. 1 is a diagram showing an energy treatment device (energy treatment system) 1. As shown in FIG. 1, the energy treatment device (medical treatment device) 1 includes an energy treatment instrument (handpiece) 2 and an energy control device (energy control unit) 3. The energy treatment instrument 2 has a longitudinal axis C. Here, one side in a direction along the longitudinal axis C is a distal side (an arrow C1 side in FIG. 1), and the side opposite to the distal side is a proximal side (an arrow C2 side in FIG. 1). The energy treatment instrument 2 is separably connected to the energy control device 3 via a cable 5. The supply of energy (ultrasonic electric energy and high-frequency electric energy) to the energy treatment instrument 2 is controlled by the energy control device 3.

As shown in FIG. 1, the energy treatment instrument 2 includes a housing 6. The housing 6 includes a housing main body 7 extending along the longitudinal axis C, and a grip (fixed handle) 8 extending from the housing main body 7 toward a direction that crosses the longitudinal axis C. A handle (movable handle) 11 is rotatably attached to the housing 6. The handle 11 opens or closes relative to the grip 8 by the rotation of the handle 11 relative to the housing 6. A rotating knob 12 is coupled to the distal side of the housing main body 7 rotatably to the housing 6 around the longitudinal axis C. An operational button (operational member) 13 with which an operational input to supply energy (treatment energy) to the energy treatment instrument 2 from the energy control device 3 is performed is attached to the housing 6.

A transducer case 15 is coupled to the housing 6 in a state to be inserted into the housing main body 7 from the proximal side. One end of the cable 5 is connected to a proximal portion of the transducer case 15. A sheath 16 is also coupled to the housing 6 in a state to be inserted into the rotating knob 12 and the housing main body 7 from the distal side. The sheath 16 extends along the longitudinal axis C. In the energy treatment instrument 2, a vibration transmitting member (probe) 17 extends toward the distal side from the inside of the housing main body 7 through the inside of the sheath 16. The vibration transmitting member 17 extends along the longitudinal axis C, and a first grasp portion (probe treatment portion) 21 is provided in a distal portion of the vibration transmitting member 17. The vibration transmitting member 17 is inserted through the sheath 16 in a state where the first grasp portion 21 protrudes toward the distal side from the distal end of the sheath 16.

A second grasp portion (jaw) 22 is rotatably attached to a distal portion of the sheath 16. When the handle 11 is opened or closed relative to the grip 8, a movable shaft (not shown) extending through the inside of the sheath 16 moves along the longitudinal axis C. Accordingly, the second grasp portion 22 rotates relative to the sheath 16, and the second grasp portion 22 and the first grasp portion 21 open or close relative to each other. In the present embodiment, an end effector 20 which conducts a treatment by use of supplied energy is configured by the first grasp portion 21 and the second grasp portion 22. In the end effector 20, a treated target such as a living tissue grasped between the first grasp portion 21 and the second grasp portion 22 is treated by the supplied energy. The sheath 16, the vibration transmitting member 17 (the first grasp portion 21), and the second grasp portion 22 rotate around the longitudinal axis C relative to the housing 6 together with the rotating knob 12 in response to the rotating of the rotating knob 12. As a result, an angular position of the end effector 20 around the longitudinal axis C is adjusted.

FIG. 2 is a diagram showing an electric connection state between the energy treatment instrument 2 and the energy control device 3, and a configuration to supply energy to the end effector 20. As shown in FIG. 2, the energy control device 3 includes a controller 25, an energy source 26, and a storage medium 27 such as a memory. The energy source 26 is capable of outputting ultrasonic electric energy (electric energy to generate ultrasonic vibration in a later-described vibration generator 40) and high-frequency electric energy (electric energy to pass a high-frequency electric current to the treated target between the first grasp portion 21 and a later-described electrode member 46). The controller 25 includes a processor or the like which includes, for example, a central processing unit (CPU) or an application specific integrated circuit (ASIC), and can exchange signals and information with the energy source 26 and the storage medium 28 via an interface such as a bus. Thus, the controller 25 is capable of detecting the output state of energy from the energy source 26, and also capable of controlling the output state of energy from the energy source 26. Moreover, the controller 25 is capable of reading information from the storage medium 27, and also capable of writing information into the storage medium 27.

A switch 31 is provided inside the housing 6. The switch 31 is electrically connected to the controller 25 via signal paths 32A and 32B extending through the inside of the housing 6 and the inside of the cable 5. The switch 31 is provided at a position where the switch 31 can be pressed by the operational button 13, and changes between on and off on the basis of the operational input in the operational button 13. The controller 25 detects whether or not the operational input is performed in the operational button 13 by sensing whether the switch 31 is on or off via the signal paths 32A and 32B. The controller 25 then controls the output state of energy from the energy source 26 on the basis of the detection result of whether or not there is an operational input in the operational button 13. In the present embodiment, the controller 25 simultaneously outputs the ultrasonic electric energy and the high-frequency electric energy from the energy source 26 by detecting that the operational input is performed in the operational button 13.

FIG. 3 is a diagram showing a configuration to control the output of energy from the energy source 26. As shown in FIG. 3, the energy source 26 includes an ultrasonic electric energy source (ultrasonic electric power source) and a high-frequency electric energy source (high-frequency electric power source) 36. The ultrasonic electric energy source 35 includes a converting circuit (driving circuit) or the like which converts, for example, electric power from a battery or electric power from an outlet into ultrasonic electric energy (ultrasonic electric power P). The controller 25 controls the output of the ultrasonic electric energy from the ultrasonic electric energy source 35 by controlling the driving of the ultrasonic electric energy source 35. The high-frequency electric energy source 36 includes a converting circuit (driving circuit) or the like which converts, for example, electric power from a battery or electric power from an outlet into high-frequency electric energy (high-frequency electric power P'). The controller 25 controls the output of the high-frequency electric energy from the high-frequency electric energy source 36 by controlling the driving of the high-frequency electric energy source 36.

The vibration generator (ultrasonic transducer) 40 is provided inside the transducer case 15. The vibration generator 40 is connected to the vibration transmitting member 17 from the proximal side inside the housing main body 7. The vibration generator 40 includes (in the present embodiment, four) piezoelectric elements 41, and ultrasonic electrodes 42A and 42B. Each of the piezoelectric elements is put between the ultrasonic electrode (first ultrasonic electrode) 42A and the ultrasonic electrode (second ultrasonic electrode) 42B. The ultrasonic electrode 42A is connected to the ultrasonic electric energy source 35 of the energy source 26 via an ultrasonic electric path (first ultrasonic electric path) 43A extending through the inside of the cable 5. The ultrasonic electrode 42B is connected to the ultrasonic electric energy source 35 via an ultrasonic electric path (second ultrasonic electric path) 43B extending through the inside of the cable 5.

The ultrasonic electric energy is output from the ultrasonic electric energy source 35 under the control of the controller 25, is thereby supplied to the vibration generator 40 via the ultrasonic electric paths 43A and 43B. Accordingly, an ultrasonic voltage V is applied across the ultrasonic electrode (first ultrasonic electrode) 42A and the ultrasonic electrode (second ultrasonic electrode) 42B, and an ultrasonic electric current I flows through the ultrasonic electric paths 43A and 43B. The ultrasonic electric current I is then converted into ultrasonic vibration by the piezoelectric elements 41, and ultrasonic vibration is generated in the vibration generator 40. The ultrasonic vibration generated in the vibration generator 40 is transmitted from the proximal side to the distal side in the vibration transmitting member 17. The first grasp portion 21 then vibrates, for example, in a direction along the longitudinal axis C by the transmission of the ultrasonic vibration to the first grasp portion 21 of the end effector 20. This permits the end effector 20 to conduct a treatment by use of the ultrasonic vibration. The ultrasonic electric current I is an alternating electric current whose flowing direction periodically changes.

FIG. 4 shows the end effector 20 through a section perpendicular to the longitudinal axis C. FIG. 4 shows a state where the first grasp portion 21 and the second grasp portion 22 are closed relative to each other. As shown in FIG. 4, the second grasp portion 22 includes a pad member (abutment member) 45 made of an electrically insulating material such as polyether ether ketone (PEEK), and the electrode member 46 made of an electrically conductive material. When the first grasp portion 21 and the second grasp portion 22 are closed relative to each other, the pad member 45 can abut on the first grasp portion 21. That is, when the second grasp portion 22 is closed relative to the first grasp portion 21 a state where no treated target is disposed between the first grasp portion 21 and the second grasp portion 22, the pad member 45 abuts on the first grasp portion 21. In a state where the pad member 45 is in abutment with the first grasp portion 21, the electrode member 46 is apart from the first grasp portion 21, and does not contact the first grasp portion 21.

As shown in FIG. 2 and FIG. 3, first grasp portion (first high-frequency electrode) 21 is connected to the high-frequency electric energy source 36 via a high-frequency electric path (first high-frequency electric path) 47A extending through the inside of the housing 6 and the inside of the cable 5. The electrode member (second high-frequency electrode) 46 of the second grasp portion 22 is connected to the high-frequency electric energy source 36 via a high-frequency electric path (second high-frequency electric path) 47B extending through the inside of the housing 6 and the inside of the cable 5.

High-frequency electric energy is output from the high-frequency electric energy source 36 under the control of the controller 25, and is thereby supplied to the first grasp portion 21 and the electrode member 46 (the second grasp portion 22) via the high-frequency electric paths 47A and 47B. Accordingly, a high-frequency voltage V' is applied across the first grasp portion 21 and the electrode member 46, and a high-frequency electric current I' flows through the high-frequency electric paths 47A and 47B. In this instance, the first grasp portion 21 and the electrode member 46 function as high-frequency electrodes of high-frequency electric energy (high-frequency electric power P') different in electric potential from each other. This permits the end effector 20 to conduct a treatment by use of the high-frequency electric energy. The high-frequency electric current I' is an alternating electric current whose flowing direction periodically changes.

As shown in FIG. 5, the controller 25 includes an impedance detector 51, a switch detector 52, and a judgment section 53. The impedance detector 51, the switch detector 52, and the judgment section 53 are each formed from, for example, an electronic circuit constituting a part of a processor, and performs a part of processing in the processor. The impedance detector 51 detects the output state of the ultrasonic electric energy from the ultrasonic electric energy source 35 with time, and thereby detects a change of the ultrasonic electric current I with time and a change of the ultrasonic voltage V with time. In this instance, a change of the ultrasonic electric power P with time may be detected. Using Equation (1), the impedance detector 51 detects (calculates), with time, acoustic impedance (ultrasonic impedance) Z as impedance in the path the ultrasonic electric energy (impedance in the vibration generator 40).

[Equation 1]

$$Z = V/I = V^2/P \qquad (1)$$

The impedance detector 51 also detects the output state of the high-frequency electric energy from the high-frequency electric energy source 36 with time, and thereby detects a change of the high-frequency electric current I' with time and a change of the high-frequency voltage V' with time. In this instance, a change of the high-frequency electric power P' with time may be detected. Using Equation (2), the impedance detector 51 detects (calculates), with time, high-frequency impedance (tissue impedance) Z' as impedance in the path of the high-frequency electric energy (impedance between the first grasp portion 21 and the electrode member 46).

[Equation 2]

$$Z' = V'/I' = V'^2/P' \qquad (2)$$

The switch detector 52 detects a switch from a gradually decreasing state where the acoustic impedance Z gradually decreases with time to a gradually increasing state where the acoustic impedance Z gradually increases with time, on the basis of the detection result of the acoustic impedance Z in the impedance detector 51. Here, the gradually decreasing state of the acoustic impedance Z is a state where the acoustic impedance Z gradually decreases with time, and also includes a state where the acoustic impedance Z gradually decreases including a slight increase and decrease. Similarly, the gradually increasing state of the acoustic impedance Z is a state where the acoustic impedance Z gradually increases with time, and also includes a state where the acoustic impedance Z gradually increases including a slight increase and decrease of.

The judgment section 53 makes judgments regarding the output of the ultrasonic electric energy and the output of the high-frequency electric energy on the basis of the detection result in the impedance detector 51 and the detection result in the switch detector 52 in a state where the ultrasonic electric energy and the high-frequency electric energy are simultaneously output from the energy source 26. For example, the judgment section 53 judges whether or not to stop the output of the ultrasonic electric energy on the basis of the detection result in the impedance detector 51 and the detection result in the switch detector 52, and also judges whether or not to stop the output of the high-frequency electric energy on the basis of the detection result in the impedance detector 51. The processing by the controller 25 including the impedance detector 51, the switch detector 52, and the judgment section 53 in a state where the ultrasonic electric energy and the high-frequency electric energy are simultaneously output from the energy source 26 will be described later in detail.

Next, functions and advantageous effects of the energy treatment device 1 according to the present embodiment are described. When treating a living tissue by use of the energy treatment device 1, a surgeon holds the housing 6 and the handle 11, and inserts the distal portion of the sheath 16 and the end. effector 20 into a body cavity such as an abdominal cavity. The surgeon then adjusts an angular position of the end effector 20 around the longitudinal axis C with the rotating knob 12, and disposes a treated target such as a living tissue (blood vessel) between the first grasp portion 21 and the second grasp portion 22. The surgeon then closes the handle 11 relative to the grip 8, and thereby closes the first grasp portion 21 and the second grasp portion 22 relative to each other and grasps the treated target between the first grasp portion 21 and the second grasp portion 22.

When an operational input is performed in the operational button (operational member) 13 in a state where the treated target is grasped in the end effector 20, the controller 25 controls the energy source 26 so that the ultrasonic electric energy and the high-frequency electric energy are simultaneously output from the energy source 26. Accordingly, ultrasonic vibration is generated in the vibration generator 40, the generated ultrasonic vibration is transmitted to the end effector 20 (the first grasp portion 21), and at the same time, the high-frequency electric energy is supplied to the end effector 20 (the first grasp portion 21 and the electrode member 46). The outputs of the ultrasonic electric energy and the high-frequency electric energy are preferably simultaneously started, but do not need to be completely simultaneously started, and there may be some time lag as long as the outputs are substantially simultaneous. That is, being "simultaneous" here not only includes being completely simultaneous but also includes being substantially simultaneous.

In the present embodiment, the end effector 20 simultaneously uses the ultrasonic vibration and the high-frequency electric energy to coagulate the treated target, and seals, for example, a blood vessel. In this instance, frictional heat is generated between the treated target pressed to the first grasp portion 21 and the first grasp portion 21 by the first grasp portion 21, which vibrate due to the ultrasonic vibration, and the pad member 45, and the treated target is coagulated by the frictional heat. The high-frequency electric current I' then flows through the treated target between the first grasp portion 21 and the electrode member 46, whereby the treated target is degenerated and coagulated.

FIG. 5 is a flowchart showing processing in the energy control device 3 based on an operational input in the operational button 13. As shown in FIG. 5, when the operational input in the operational button 13 is detected, the controller 25 starts simultaneous outputs of the ultrasonic electric energy (indicated as US in FIG. 5) and the high-frequency electric energy (indicated as HF in FIG. 5) from the energy source 26 (step S101). The controller 25 then starts phase locked loop (PLL) control regarding the ultrasonic electric energy (step S102). Due to the PLL control, the frequency of the ultrasonic electric current I is adjusted, and a resonance frequency Fr of the ultrasonic vibration is adjusted. In this instance, for example, the resonance frequency Fr of the ultrasonic vibration is adjusted to a frequency that minimizes the acoustic impedance Z in a predetermined frequency range.

When the PLL control is started, the impedance detector 51 (the controller 25) starts the detection of the acoustic impedance Z and high-frequency impedance Z' (step S103). Accordingly, a change of the acoustic impedance Z with time and a change of the high-frequency impedance Z' with time are detected. In this instance, the ultrasonic electric current I and the ultrasonic voltage V (the ultrasonic electric power P) are detected with time, and the acoustic impedance Z is calculated by use of Equation (1). Further, the high-frequency electric current I' and the high-frequency voltage V' (the high-frequency electric power P') are detected with time, and the high-frequency impedance Z' is calculated by use of Equation (2).

Here, a time t in which the start time of the PLL control is zero is set as a variable, and acoustic impedance $Z(t)$ and high-frequency impedance $Z'(t)$ at the time t are defined. A minimum impedance value Zmin is defined as a minimum value of the acoustic impedance Z before the time t at and after the start time of the PLL control. When the detection of the acoustic impedance Z is started, the controller 25 (the switch detector 52) judges whether or not the acoustic impedance Z(t) at the time t is higher than the minimum impedance value Zmin on the basis of the detection result of the acoustic impedance (ultrasonic impedance) Z (step S104). When the acoustic impedance Z(t) at the time t is less than or equal to the minimum impedance value Zmin (step S104—No), the controller 25 (the switch detector 52) updates the acoustic impedance Z(t) at the time t as the minimum impedance value Zmin (step S105). After the processing in step S105 is performed, the processing returns to step S104. The controller 25 then again makes a judgment in step S104 using the updated minimum impedance value Zmin after the time when the acoustic impedance Z is at the minimum impedance value Zmin updated in step S105.

When the acoustic impedance Z(t) at the time t is higher than the minimum impedance value Zmin in step S104 (step S104—Yes), the controller 25 (the judgment section 53) judges whether or not a value which is a result of the subtraction of the minimum impedance value Zmin from the acoustic impedance Z(t) is equal to or more than a reference difference value ΔZth (step S106). That is, if the sum of the minimum impedance value Zmin and the reference difference value ΔZ is a reference impedance value Zth, the controller 25 judges whether or not the acoustic impedance Z(t) at the time t is equal to or more than the reference impedance value Zth. Therefore, whether or not Equation (3) is satisfied is judged by the judgment in step S106. The reference difference value ΔZth and the reference impedance value Zth are set on the basis of the value of the minimum impedance value Zmin, how the acoustic impedance Z changes, and others, and in a certain example, the reference difference value ΔZth is set within a range of 50 Ω or more to 60 Ω or less.

[Equation 3]

$$Z(t) \geq Zth \qquad (3)$$

When the value which is the result of the subtraction of the minimum impedance value Zmin from the acoustic impedance Z(t) is lower than the reference difference value ΔZth (step S106—No), the processing returns to step S104. The controller 25 then again makes a judgment in step S104 after the time the judgment target for step S106. In contrast, when the value which is the result of the subtraction of the minimum impedance value Zmin from the acoustic impedance Z(t) is equal to or more than the reference difference value ΔZth (step S106—Yes), the controller 25 stops the output of the ultrasonic electric energy (US) from the energy source 26 (the ultrasonic electric energy source 35) (step S107). Accordingly, the ultrasonic vibration is no longer transmitted to the end effector 20 (the first grasp portion 21).

When the output of the ultrasonic electric energy is stopped, the controller 25 (the judgment section 53) judges on the basis of the detection result of the high-frequency impedance Z' whether or not the high-frequency impedance Z'(t) at the time t is equal to or more than a set threshold (high-frequency threshold) Z'th (step S108). When the high-frequency impedance Z'(t) is lower than the threshold Z'th (S108—No), the processing returns to step S108. The controller 25 then again makes a judgment in step S108 after the time of the judgment target for step S108. In contrast, when the high-frequency impedance Z'(t) is equal to or more than the threshold Z'th (S108—Yes), the controller 25 stops the output of the high-frequency electric energy (HF) from the energy source 26 (the high-frequency electric energy source 36) (step S109). Accordingly, the high-frequency electric energy is no longer supplied to the end effector 20 (the first grasp portion 21 and the electrode member 46). The threshold Z'th is set on the basis of how the high-frequency impedance Z changes, and others.

Figure 6:
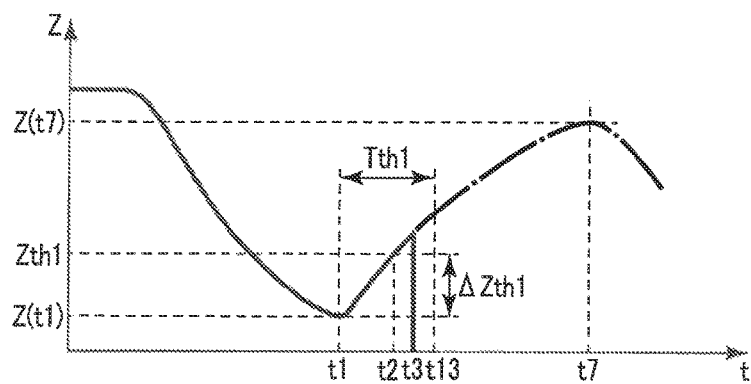
FIG. 6 is a schematic diagram showing an example of a change of acoustic impedance with time after the outputs of ultrasonic electric energy and high-frequency electric energy are simultaneously started.
Figure 7:
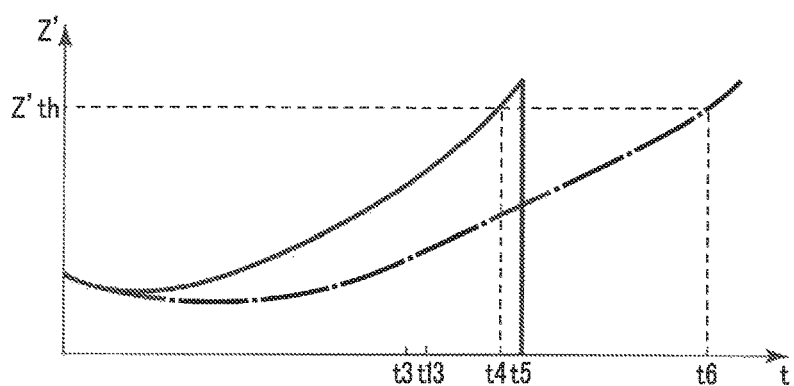
FIG. 7 is a schematic diagram showing an example of a change of high-frequency impedance with time after the outputs of ultrasonic electric energy and high-frequency electric energy are simultaneously started.

FIG. 6 shows an example of a change of the acoustic impedance Z with time after the outputs of the ultrasonic electric energy and the high-frequency electric energy are simultaneously started. FIG. 7 is a diagram showing an example of a change of the high-frequency impedance Z' with time after the outputs of the ultrasonic electric energy and the high-frequency electric energy are simultaneously started. In FIG. 6 and FIG. 7, the time t in which the start time of the PLL control is zero is indicated on the abscissa axis. The acoustic impedance Z is indicated on the ordinate axis in FIG. 6, and the high-frequency impedance Z' is indicated on the ordinate axis in FIG. 7. In one example, after the outputs of the ultrasonic electric energy and the high-frequency electric energy are simultaneously started, the acoustic impedance Z changes as indicated by a solid line in FIG. 6, and the high-frequency impedance Z' changes as indicated by a solid line in FIG. 7.

As shown in FIG. 6, after some time from the start of the PLL control, the resonance frequency Fr of the ultrasonic vibration is adjusted by the PLL control, and the acoustic impedance Z starts to gradually decrease with time. The gradually decreasing state where the acoustic impedance Z gradually decreases with time continues for a while. If the first grasp portion 21 vibrates for a while due to the ultrasonic vibration, the temperature of the treated target rises to a certain degree due to frictional heat generated between the first grasp portion 21 and the treated target, and the state of the treated target changes (i.e. the treated target hardens). The change of the state of the treated target leads to a switch from the gradually decreasing state where the acoustic impedance Z gradually decreases with time to the gradually increasing state where the acoustic impedance Z gradually increases with time. The gradually increasing state of the acoustic impedance Z continues for a while. In one example in FIG. 6, the acoustic impedance Z switches from the gradually decreasing state to the gradually increasing state at a time t1.

After the outputs of the ultrasonic electric energy and the high-frequency electric energy are started, frictional heat generated by the ultrasonic vibration and heat generated by the high-frequency electric energy act on the treated target, and water in the treated target evaporates. Thus, as shown in FIG. 7, if the output of the high-frequency electric energy is started, the high-frequency impedance Z' slightly decreases and then keeps gradually increasing. If the high-frequency impedance Z' rises to a certain degree of value (e.g. the threshold Z'th), the treated target will be in a state of suitable coagulation.

In the present embodiment, the energy control device 3 performs the processing shown in FIG. 5 on the basis of the operational input in the operational button 13. Therefore, when the acoustic impedance Z changes as indicated by the solid line in FIG. 6, the processing in steps S104 and S105 is repeated with time by the controller 25 (the switch detector 52) in the gradually decreasing state of the acoustic impedance Z before the time t1. That is, in the gradually decreasing state of the acoustic impedance before the time t1, the processing of updating (setting) the acoustic impedance Z(t) at the time t as the minimum impedance value Zmin is continued. Acoustic impedance Z(t1) at the time t1 is then set as the minimum impedance value Zmin.

In the gradually increasing state of the acoustic impedance Z after the time t1, the acoustic impedance Z(t) at the time t is higher than the acoustic impedance Z(t1) set as the minimum impedance value Zmin. Thus, the acoustic impedance Z(t1) at the time t1 is continuously held as the minimum impedance value Zmin. The controller 25 (the switch detector 52) detects that the acoustic impedance Z has switched from the gradually decreasing state to the gradually increasing state at the time t1, on the basis of the fact that the acoustic impedance Z(t1) is held as the minimum impedance value Zmin.

When the switch of the acoustic impedance Z to the gradually increasing state at the time t1 is detected, the controller 25 (the judgment section 53) sets the reference difference value ΔZth and the reference impedance value Zth. When the acoustic impedance Z changes as indicated by the solid line in FIG. 6, a reference difference value ΔZth1 and a reference impedance value Zth1 are set. Here, the reference impedance value Zth1 is the sum of the acoustic impedance Z(t1) at the time t1 and the reference difference value ΔZth1, and is higher than the acoustic impedance Z(t1) at the time t1. In the gradually increasing state of the acoustic impedance after the time t1, the processing in step S104, and the processing in step S106 using the set reference difference value ΔZth1 and reference impedance value Zth1 are repeated with time.

By the processing in step S106, the controller 25 (the judgment section 53) then detects that acoustic impedance Z(t2) at a time t2 is the same as the reference impedance value Zth1. That is, the controller 25 (the judgment section 53) detects that a value which is a result of the subtraction of the acoustic impedance Z(t1) at the time t1 set as the minimum impedance value Zmin from the acoustic impedance Z(t2) at the time t2 is the same as the reference difference value ΔZth1. Consequently, the controller 25 (the judgment section 53) judges that the acoustic impedance Z has reached the reference impedance value Zth1 at the time t2.

By the processing in step S107, the controller 25 stops the output of the ultrasonic electric energy (US) from the energy source 26 at the time t2 or at a time t3 immediately after the time t2. Therefore, in the present embodiment, the controller 25 stops the output of the ultrasonic electric energy on the basis of the detection of the switch of the acoustic impedance Z from the gradually decreasing state to the gradually increasing state at the time t1 and on the basis of the fact that the acoustic impedance Z reaches the reference impedance value Zth1 at the time t2 after the switch to the gradually increasing state. That is, the output of the ultrasonic electric energy is stopped the basis of the change of the acoustic impedance Z with time from the acoustic impedance Z(t1) set as the minimum impedance value Zmin at and after the time t1 of the switch to the gradually increasing state. The controller 25 then stops the output of the ultrasonic electric energy at and after the time t1 which is the time of the switch to the gradually increasing state and while the acoustic impedance Z is in the gradually increasing state.

Even after the output of the ultrasonic electric energy is stopped at the time t2 or t3, the high-frequency electric energy is continuously output. After the time t3, the controller 25 (the judgment section 53) repeats the processing in step S108 with time by use of the set threshold Z'th. When the high-frequency impedance Z' changes as indicated by the solid line in FIG. 7, a threshold (high-frequency threshold) Z'1th is set. Therefore, after the time t3, whether or not high-frequency impedance Z'(t) at the time t is equal to or more than a threshold Z'th1 is continuously judged.

By the processing in step S108, the controller 25 (the judgment section 53) then detects that high-frequency impedance Z'(t4) at a time t4 is the same as the threshold Z'th1. Consequently, the controller 25 (the judgment section 53) judges that the high-frequency impedance Z' has reached the threshold Z'th1 at the time t4.

By the processing in step S109, the controller 25 stops the output of the high-frequency electric energy (HF) from the energy source 26 at the time t4 or at a time t5 immediately after the time t4. Therefore, in the present embodiment, the controller 25 stops the output of the high-frequency electric energy on the basis of the fact that the high-frequency impedance Z' reaches the threshold Z'th1 at the time t4.

Here, a change of the high-frequency impedance Z' with time in the case where no ultrasonic electric energy is output and the high-frequency electric energy alone is output is indicated by a long dashed dotted line in FIG. 7. In this case, because the frictional heat resulting from the ultrasonic vibration is not generated, it requires a long time before the temperature of the treated target rises to a certain degree, and it requires a long time before the high-frequency impedance Z' reaches the threshold Z'th (Z'th1).

In contrast, in the present embodiment, the output of the ultrasonic electric energy is started simultaneously with the high-frequency electric energy, so that in addition to the heat generated by the high-frequency electric energy, the frictional heat generated by the ultrasonic vibration acts on the treated target. Thus, the temperature of the treated target rapidly rises, and the high-frequency impedance Z' rapidly reaches the threshold Z'th. Actually, as shown in FIG. 7, when the high-frequency electric energy alone is output, the high-frequency impedance Z' reaches the threshold Z'th1 at a time t6, whereas when the outputs of the ultrasonic electric energy and the high-frequency electric energy are simultaneously started as in the present embodiment, the high-frequency impedance Z' reaches the threshold Z'th1 at the time t4 before the time t6. Due to the rapid rise of the temperature of the treated target, the treated target is rapidly coagulated after the output of the high-frequency electric energy is started, and a blood vessel or the like can be rapidly sealed. When the high-frequency electric energy alone is output, it requires about 5 seconds from the start of the output of the energy before the high-frequency impedance Z' reaches the threshold Z'th, whereas when the outputs of the ultrasonic electric energy and the high-frequency electric energy are simultaneously started, the high-frequency impedance Z' reaches the threshold Z'th in about 3 seconds from the start of the output of the energy.

A change of the acoustic impedance Z in the case where the output of the ultrasonic electric energy is not stopped at the time t2 or t3 and the output of the ultrasonic electric energy is continued even after the time t3 is indicated by a long dashed dotted line in FIG. 6. If the output of the ultrasonic electric energy is continued after the time t3, the treated target starts to be partly cut apart by the frictional heat resulting from the ultrasonic vibration. Because the treated target is partly cut apart, the pad member 45 of the second grasp portion 22 contacts the first grasp portion 21 which vibrates due to the ultrasonic vibration, and the pad member 45 is denatured by the frictional heat. As a result of the denaturing of the pad member 45, the acoustic impedance Z switches from the gradually increasing state to the gradually decreasing state, and a peak (local maximum) of the acoustic impedance Z with time is produced. Actually, as shown in FIG. 6, when the output of the ultrasonic electric energy is continued after the time t3, the acoustic impedance Z switches from the gradually increasing state to the gradually decreasing state at a time t7, and a peak of the acoustic impedance Z is produced. That is, acoustic impedance Z(t7) at the time t7 will be a peak value of the acoustic impedance Z. After some time from the production of the peak of the acoustic impedance Z, the treated target is completely cut apart.

In the present embodiment, the switch of the acoustic impedance Z from the gradually decreasing state to the gradually increasing state is detected, and the production of a local minimum (valley) in the change of the acoustic impedance Z with time is detected. On the basis of at least the fact that the production of the local minimum (valley) in the change of the acoustic impedance Z with time is detected, the output of the ultrasonic electric energy from the energy source 26 is rapidly stopped. Thus, the output of the ultrasonic electric energy is stopped during the gradually increasing state of the acoustic impedance Z at and after the switch of the acoustic impedance Z to the gradually increasing state, and the output of the ultrasonic electric energy is stopped before the peak of the acoustic impedance Z with time is produced (e.g. before the time t7). Consequently, even when the treated target is coagulated by use of the ultrasonic vibration as well as the high-frequency electric energy, the treated target is not cut apart by the frictional heat resulting from the ultrasonic vibration, and the treated target can be suitably coagulated (sealed).

In the present embodiment, the output of the ultrasonic electric energy is stopped on the basis of the fact that the acoustic impedance Z reaches the reference impedance value Zth at and after the switch to the gradually increasing state. Here, in one example, the acoustic impedance (e.g. Z(t1)) is about 1300 Ω at the time of the local minimum (e.g. t1) when the acoustic impedance Z switches from the gradually decreasing state to the gradually increasing state, and the acoustic impedance (e.g. Z(t7)) is about 1450 Ω at the time of the peak (e.g. t7) when the acoustic impedance Z switches from the gradually increasing state to the gradually decreasing state after the time of the local minimum. In this case, the acoustic impedance at the time of the peak (e.g. Z(t7)) is about 150 Ω higher than the acoustic impedance at the time of the local minimum (e.g. Z(t1)). Actually, the difference between the acoustic impedance at the time of the peak (e.g. Z(t7)) and the acoustic impedance at the time of the local minimum (e. g. Z(t1)) is about 135 Ω at the minimum. In the present embodiment, the reference difference value ΔZth is set to a range of 50 Ω or more to 135 Ω or less, and the reference impedance value Zth is a value in which the reference difference value ΔZth is added to the acoustic impedance (e.g. Z(t1)) at the time of the local minimum (The time of the switch to the gradually increasing state). Thus, the output of the ultrasonic electric energy is stopped on the basis of the fact that the acoustic impedance Z reaches the reference impedance value Zth, whereby the output of the ultrasonic electric energy is certainly stopped before the production of the peak of the acoustic impedance Z. Consequently, it is also possible to certainly prevent the treated target from being cut apart by the frictional heat.

Figure 8:
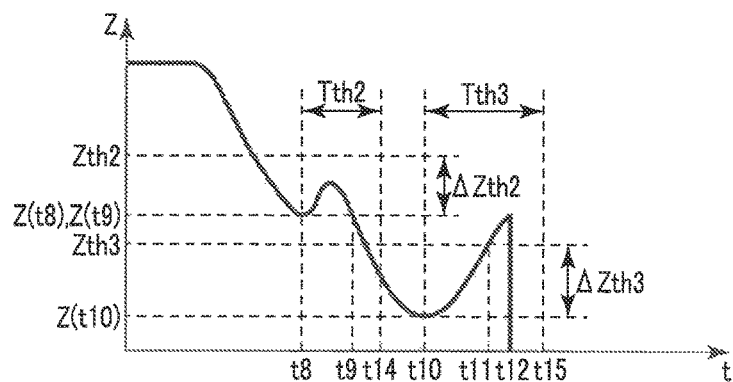
FIG. 8 is a schematic diagram showing an example different from that in FIG. 6 of a change of the acoustic impedance with time after the outputs of ultrasonic electric energy and high-frequency electric energy are simultaneously started.

FIG. 8 is a diagram showing an example different from that in FIG. 6 of a change of the acoustic impedance Z with time after the outputs of the ultrasonic electric energy and the high-frequency electric energy are simultaneously started. In FIG. 8, the time t in which the start time of the PLL control is zero is indicated on the abscissa axis, and the acoustic impedance Z is indicated on the ordinate axis. In one example in FIG. 8 as well, the state of the treated target changes due to the rise of the temperature of the treated target to a certain degree. Thus, at a time t10, the acoustic impedance Z switches from the gradually decreasing state to the gradually increasing state, and a local minimum of the acoustic impedance Z is produced. However, depending on the situation of the treatment or the like, the acoustic impedance z switches from the gradually decreasing state to the gradually increasing state, and a local minimum of the acoustic impedance Z is produced at a time t8 before the time t10, as shown in one example in FIG. 8. That is, a local minimum (a switch from the gradually decreasing state to the gradually increasing state) of the acoustic impedance Z may be generated before the time (e.g. t10) when the local minimum of the acoustic impedance Z is produced due to the change of the state of the treated target resulting from the rise of the temperature of the treated target. In one example in FIG. 8, after the acoustic impedance Z becomes the local minimum at the time t8, the acoustic impedance Z again starts to gradually decrease, and the acoustic impedance Z keeps gradually decreasing before the time t10.

In the present embodiment, the energy control device 3 performs the processing shown in FIG. 5 on the basis of the operational input in the operational button 13. Therefore, when the acoustic impedance Z changes as shown in FIG. 8, the processing in steps S104 and S105 is repeated with time by the controller 25 (the switch detector 52) in the gradually decreasing state of the acoustic impedance Z before the time t8. The controller 25 (the switch detector 52) then sets acoustic impedance Z(t8) at the time t8 as the minimum impedance value Zmin, and detects that the acoustic impedance Z has switched from the gradually decreasing state to the gradually increasing state at the time t8. In this instance, the controller 25 (the judgment section 53) sets a reference difference value ΔZth2 and a reference impedance value Zth2. After the time t8, the processing in step S104, and the processing it step S106 using the set reference difference value ΔZth2 and reference impedance value Zth2 are repeated with time.

When the acoustic impedance Z changes as shown in FIG. 8, the controller 25 judges that acoustic impedance Z(t9) at a time t9 has become less than or equal to the acoustic impedance Z(t8) set as the minimum impedance value Zmin as result of the processing in step S104. The acoustic impedance Z(t9) at the time t9 is then updated as the minimum impedance value Zmin by the processing in step S105. When the minimum impedance value Zmin is updated to the acoustic impedance Z(t9), the processing in steps S104 and S105 is repeated with time in the gradually decreasing state of the acoustic impedance Z from the time t9 to the time t10. The controller 25 (the switch detector 52) then updates acoustic impedance Z(t10) at the time t10 as the minimum impedance value Zmin, and detects that the acoustic impedance Z has switched from the gradually decreasing state to the gradually increasing state at the time t10. In this instance, the controller 25 (the judgment section 53) sets a reference difference value ΔZth3 and a reference impedance value Zth3. After the time t10, the processing in step S104, and the processing in step S106 using the set reference difference value ΔZth3 and reference impedance value Zth3 are repeated with time.

By the processing in step S106, the controller 25 (the judgment section 53) then detects that acoustic impedance Z(t11) at a time t11 is the same as the reference impedance value Zth3, and judges that the acoustic impedance Z has reached the reference impedance value Zth3 at the time t11. By the processing in step S107, the controller 25 stops the output of the ultrasonic electric energy (US) from the energy source 26 at the time t11 or at a time t12 immediately after the time t11.

As described above, in the present embodiment, the controller 25 (the judgment section 53) judges whether or not to stop the output of the ultrasonic electric energy on the basis of the change of the acoustic impedance Z with time from the first impedance value (e.g. Z(t8)) set as the minimum impedance value Zmin at and after the switch to the gradually increasing state. When detecting that the acoustic impedance Z reaches the second impedance value (e.g. Z(t10)) less than or equal to the first impedance value (e.g. Z(t8)) set as the minimum impedance value Zmin at and after the switch to the gradually increasing state, the controller 25 (the switch detector 52) updates the minimum impedance value Zmin to the second impedance value (e.g. Z(t10)). The controller 25 (the judgment section 53) then judges whether or not to stop the output of the ultrasonic electric energy on the basis of the change of the acoustic impedance Z with time from the second impedance value (e.g. Z(t10)) updated as the minimum impedance value Zmin of the acoustic impedance Z at and after the time (t10) when the acoustic impedance Z reaches the second impedance value (e.g. Z(t10)).

Therefore, in the present embodiment, even when the acoustic impedance Z changes as shown in FIG. 8, the output of the ultrasonic electric energy is not stopped on the basis of the local minimum (the switch from the gradually decreasing state to the gradually increasing state) of the acoustic impedance Z that occurs at the time (e.g. t8) before the state of the treated target changes due to the rise of the temperature of the treated target. Thus, even when the acoustic impedance Z changes as shown in FIG. 8, the local minimum (the switch from the gradually decreasing state to the gradually increasing state) of the acoustic impedance Z resulting from the change of the state of the treated target due to the rise of the temperature of the treated target is properly detected, and the output of the ultrasonic electric energy is stopped on the basis of the change of the acoustic impedance Z with time from the impedance value (e.g. Z(t10)) at the time of the local minimum resulting from the change of the state of the treated target. Therefore, the output of the ultrasonic electric energy can be stopped by suitable timing at and after the change of the state of the treated target due to the rise of the temperature of the treated target.

(Modifications)

Figure 9:
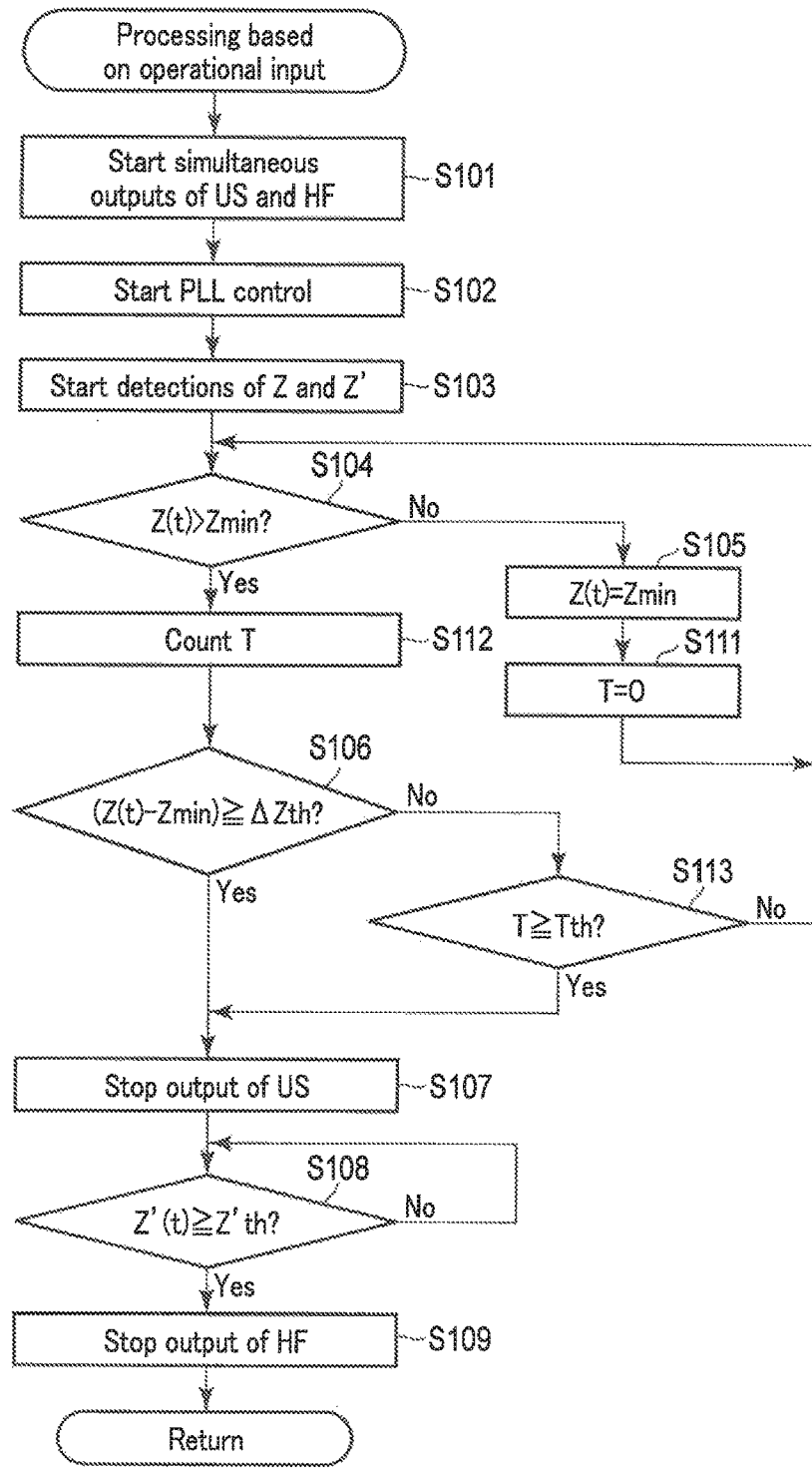
FIG. 9 is a flowchart showing processing in the energy control device based on an operational input in the operational button according to a first modification.

In a first modification, the energy control device 3 performs the processing shown in FIG. 9 on the basis of the operational input in the operational button 13. In the present modification, processing in steps S111 and S113 is performed in addition to the processing (steps S101 and S109) performed in the first embodiment. Here, when a switch time of the acoustic impedance Z from the gradually decreasing state to the gradually increasing state is detected, a count time T in which the switch time is zero is defined. In the present modification, when the acoustic impedance Z(t) at the time t is less than or equal to the minimum impedance value Zmin in step S104 (step S104—NO), the controller 25 (the switch detector 52) updates the acoustic impedance Z(t) at the time t as the minimum impedance value Zmin (step S105), and holds the count time T at zero or resets the count time T to zero (step S111). After the processing in step S111 is performed, the processing returns to step S104. The controller 25 then again makes a judgment in step S104 using the updated minimum impedance value Zmin after the time when the acoustic impedance Z is at the minimum impedance value Zmin updated in step S105.

When the acoustic impedance Z(t) at the time t is higher than the minimum impedance value Zmin in step S104 (step S104—Yes), the controller 25 (the judgment section 53) starts or continues the counting of the count time T (step S112). The count time T is not counted in a state where the processing in steps S104, S105, and S111 is repeated with time. After the processing in step S112 is performed, the controller 25 (the judgment section 53) performs the processing in step S106 described above in the first embodiment. That is, whether or not a value which is a result of the subtraction of the minimum impedance value Zmin from the acoustic impedance Z(t) is equal to or more than a reference difference value ΔZth (whether or not the acoustic impedance Z(t) at the time t is equal to or more than the reference impedance value Zth) is judged (step S106).

When the value which is the result of the subtraction. of the minimum impedance value Zmin from the acoustic impedance Z(t) is lower than the reference difference value ΔZth (step S106—No), the controller 25 (the judgment section 53) judges whether or not the count time T is equal to or more than a predetermined set time Tth (step S113). That is, whether or not the predetermined set time Tth has elapsed since the switch of the acoustic impedance Z to the gradually increasing state is judged. The predetermined set time Tth is set on the basis of the value of the minimum impedance value Zmin, how the acoustic impedance Z changes, and others.

When the count time T at the time t is less than the predetermined set time Tth (step S113—No), the processing returns to step S104 The controller 25 then again makes a judgment in step S104 after the times of the judgment targets for step S106 and step S113. In contrast, when the count time T at the time t is equal to or more than the predetermined set time Tth (step S113—Yes), the controller 25 stops the output of the ultrasonic electric energy (US) from the energy source 26 (the ultrasonic electric energy source 35) (step S107). When the value which is the result of the subtraction of the minimum impedance value Zmin from the acoustic impedance Z(t) is equal to or more than the reference difference value ΔZth in step S106 (step S106—Yes), the controller 25 also stops the output of the ultrasonic electric energy (US) from the energy source 26 (step S107). In the present modification as well, after the output of the ultrasonic electric energy is stopped, the output of the high-frequency electric energy (HF) is stopped on the basis of the fact that the high-frequency impedance Z'(t) has become equal to or more than the threshold Z'th.

In the present modification, the energy control device 3 performs the processing shown in FIG. 9 on the basis of the operational input in the operational button 13. Thus, when the acoustic impedance Z changes as indicated by the solid line in FIG. 6, the controller 25 (the switch detector 52) sets the acoustic impedance Z(t1) at the time t1 as the minimum impedance value Zmin, and detects that the acoustic impedance Z has switched from the gradually decreasing state to the gradually increasing state at the time t1, as in the first embodiment. In this instance, in the present modification, the controller 25 (the judgment section 53) sets the reference difference value ΔZth1 and the reference impedance value Zth1, and also sets a predetermined set time Tth1. The count time T in which the time t1 that is the switch time of the acoustic impedance Z to the gradually increasing state is zero is counted by the processing in step S112. After the time t1, the processing in steps S104 and S112, the processing in step S106 using the set reference difference value ΔZth1 and reference impedance value Zth1, and the processing in step S113 using the predetermined set time Tth1 are repeated with time.

By the processing in step S106, the controller 25 (the judgment section 53) then detects that the acoustic impedance Z(t2) at the time t2 is the same as the reference impedance value Zth1, and judges that the acoustic impedance Z has reached the reference impedance value Zth1 at the time t2. By the processing in step S107, the controller 25 stops the output of the ultrasonic electric energy (US) from the energy source 26 at the time t2 or at the time t3 immediately after the time t2. When the acoustic impedance Z changes as indicated by the solid line in FIG. 6, the output of the ultrasonic electric energy is stopped before a time t13 when the predetermined set time Tth1 elapses from the switch time (i.e. the time t1) of the acoustic impedance Z.

When the acoustic impedance Z changes as shown in FIG. 8, the controller 25 (the switch detector 52) sets the acoustic impedance Z(t8) at the time t8 as the minimum impedance value Zmin, and detects that the acoustic impedance Z has switched from the gradually decreasing state to the gradually increasing state at the time t8, as in the first embodiment. In this instance, in the present modification, the controller 25 (the judgment section 53) sets the reference difference value ΔZth2 and the reference impedance value Zth2, and also sets a predetermined set time Tth2. The count time T in which the time t8 that is the switch time of the acoustic impedance Z to the gradually increasing state is zero is counted by the processing in step S112. After the time t8, the processing in steps S104 and S112, the processing in step S106 using the set reference difference value ΔZth2 and reference impedance value Zth2, and the processing in step S113 using the predetermined set time Tth2 are repeated with time.

When the acoustic impedance Z changes as shown in FIG. 8, the controller 25 judges that the acoustic impedance Z has not reached the reference impedance value Zth2 before the elapse of the predetermined set time Tth2 from the time t8 at which the acoustic impedance Z switches to the gradually increasing state, by the repetition of the processing in steps S104, S112, S106, and S113. The controller 25 also judges that the acoustic impedance Z(t9) has become less than or equal to the acoustic impedance Z(t8) set as the minimum impedance value Zmin before a time t14 which is the time when the predetermined set time Tth2 elapses from the time t8. The acoustic impedance Z(t9) at the time t9 is updated as the minimum impedance value Zmin by the processing in S105, and the count time T is reset to zero by the processing in S111. The processing in steps S104, S105, and S111 is repeated with time in the gradually decreasing state of the acoustic impedance Z from the time t9 to the time t10. The controller 25 (the switch detector 52) then updates acoustic impedance Z(t10) at the time t10 as the minimum impedance value Zmin, and detects that the acoustic impedance Z has switched from the gradually decreasing state to the gradually increasing state at the time t10. In this instance, the controller 25 (the judgment section 53) sets the reference difference value ΔZth3 and the reference impedance value Zth3, and sets a predetermined set time Tth3. The count time T in which the time t10 that is the switch time of the acoustic impedance Z to the gradually increasing state is zero is counted by the processing in step S112. After the time t10, the processing in steps S104 and S112, the processing in step S106 using the set reference difference value ΔZth3 and reference impedance value Zth3, and the processing in step S113 using the predetermined set time Tth3 are repeated with time.

By the processing in step S106, the controller 25 (the judgment section 53) then detects that the acoustic impedance Z(t11) at the time t11 is the same as the reference impedance value Zth3, and judges that the acoustic impedance Z has reached the reference impedance value Zth3 at the time t11. By the processing in step S107, the controller 25 stops the output of the ultrasonic electric energy (US) from the energy source 26 at the time t11 or at the time t12 immediately after the time t11. When the acoustic impedance Z changes as shown in FIG. 8, the output of the ultrasonic electric energy is stopped before a time t15 when the predetermined set time Tth3 elapses from the switch time (i.e. the time t10) of the acoustic impedance Z.

FIG. 10 is a diagram showing an example different from those in FIG. 6 and FIG. 8 of a change of the acoustic impedance Z with time after the outputs of the ultrasonic electric energy and the high-frequency electric energy are simultaneously started. In FIG. 10, the time t in which the start time of the PLL control is zero is indicated on the abscissa axis, and the acoustic impedance Z is indicated on the ordinate axis. In one example in FIG. 10 as well, the state of the treated target changes due to the rise of the temperature of the treated target to a certain degree. Thus, at a time t16, the acoustic impedance Z switches from the gradually decreasing state to the gradually increasing state, and a local minimum of the acoustic impedance Z is produced. However, depending on the situation of the treatment or the like, the acoustic impedance Z may hardly increase after the production of the local minimum at the time t16, as shown in one example in FIG. 10.

In the present modification, the energy control device 3 performs the processing shown in FIG. 9 on the basis of the operational input in the operational button 13. Thus, when the acoustic impedance Z changes as shown in FIG. 10, the processing in steps S104, S105, and S111 is repeated with time by the controller 25 (the switch detector 52) in the gradually decreasing state of the acoustic impedance Z before the time t16. The controller 25 (the switch detector 52) then sets acoustic impedance Z(t16) at the time t16 as the minimum impedance value Zmin, and detects that the acoustic impedance Z has switched from the gradually decreasing state to the gradually increasing state at the time t16. In this instance, the controller 25 (the judgment section 53) sets a reference difference value ΔZth4 and a reference impedance value Zth4, and sets a predetermined set time Tth4. The count time T in which the time t16 that is the switch time of the acoustic impedance Z to the gradually increasing state is zero is counted by the processing in step S112. After the time t16, the processing in steps S104 and S112, the processing in step S106 using the set reference difference value ΔZth4 and reference impedance value Zth4, and the processing in step S113 using the predetermined set time Tth4 are repeated with time.

Here, when the acoustic impedance Z changes as shown in FIG. 10, the acoustic impedance Z hardly increases from the time t16 which is the time of the switch to the gradually increasing state, so that the acoustic impedance Z does not reach the reference impedance value Zth4. However, until the predetermined set time Tth4 elapses from the time t16 (i.e. from the time t16 to a time t17), the acoustic impedance Z does not become less than or equal to the acoustic impedance Z (t16) set as the minimum impedance value Zmin. Thus, the controller 25 (the judgment section 53) judges by the processing in steps S104 and S113 that the acoustic impedance Z is continuously kept at a value higher than the minimum impedance value Zmin (i.e. the impedance value Z(t16)) before the predetermined set time Tth4 elapses from the time (i.e. t16) when the acoustic impedance Z switches to the gradually increasing state. By the processing in step S107, the controller 25 stops the output of the ultrasonic electric energy (US) from the energy source 26 at the time t17 or at a time t18 immediately after the time t17.

As described above, in the present embodiment as well as in the first embodiment, the controller 25 stops the output of the ultrasonic electric energy on the basis of the detection of the switch of the acoustic impedance Z from the gradually decreasing state to the gradually increasing state at the time t1 and on the basis of the fact that the acoustic impedance Z reaches the reference impedance value Zth1 at the time t2 at and after the switch to the gradually increasing state. Thus, functions and advantageous effects similar to those in the first embodiment are provided in the present modification as well.

Furthermore, in the present modification, the controller 25 stops the output of the ultrasonic electric energy on the basis of the detection of the switch of the acoustic impedance Z from the gradually decreasing state to the gradually increasing state at the time t16 and on the basis of the fact that the acoustic impedance Z is continuously kept at a value higher than the minimum impedance value Zmin before the predetermined set time Tth4 elapses from the time (i.e. the time t16) when the acoustic impedance Z switches to the gradually increasing state. That is, in the present modification, on the basis of at least the elapse of the predetermined set time Tth4 from the time (i.e. the time t16) when the acoustic impedance Z switches to the gradually increasing state, the output of the ultrasonic electric energy is stopped.

Therefore, in the present modification, even when the acoustic impedance Z changes as shown in FIG. 10, the output of the ultrasonic electric energy can be stopped by suitable timing at and after the change of the state of the treated target due to the rise of the temperature of the treated target. That is, even when the acoustic impedance Z hardly increases after the acoustic impedance Z switches to the gradually increasing state, it is possible to certainly prevent the treated target from being cut apart by the frictional heat.

Figure 11:
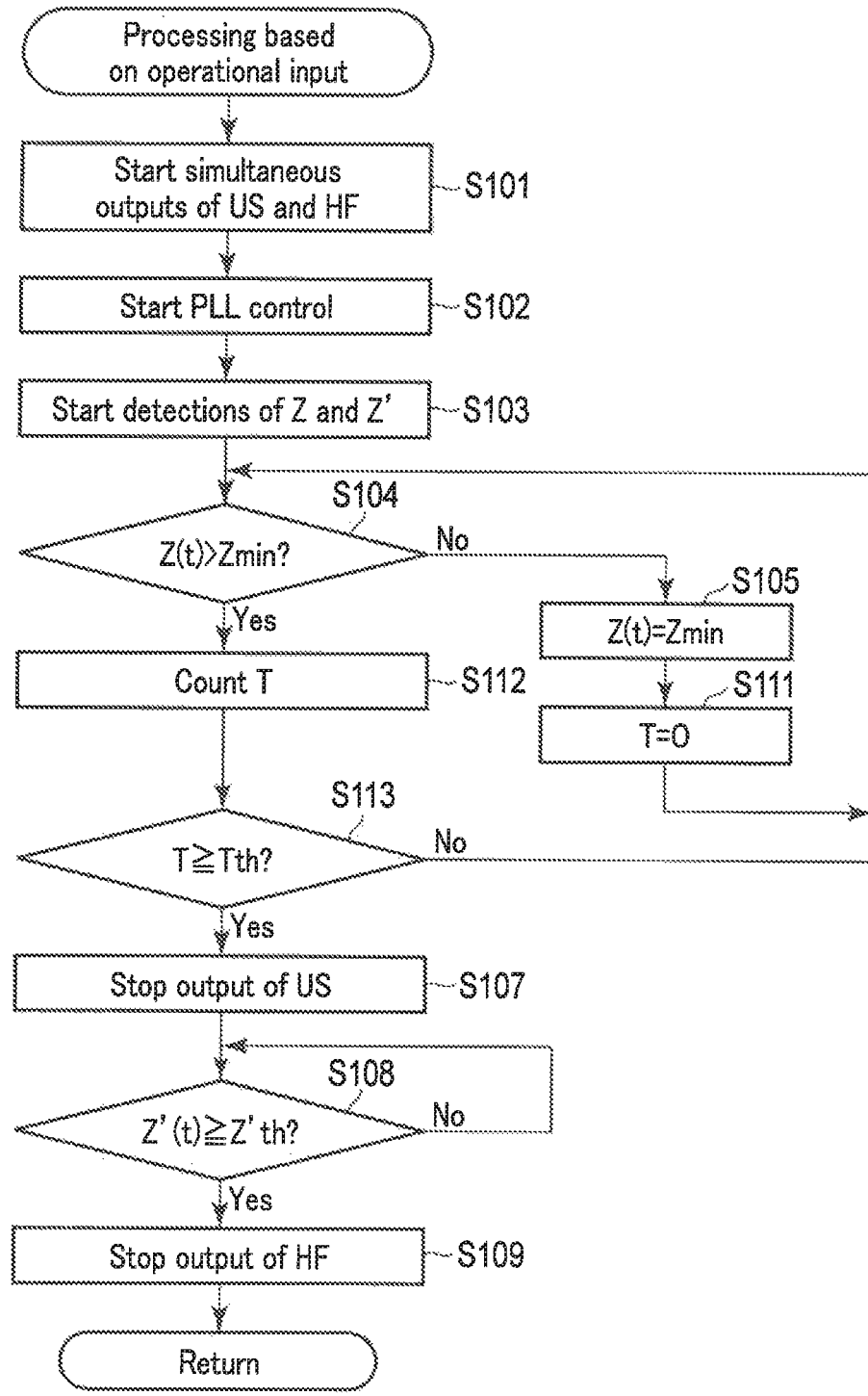
FIG. 11 is a flowchart showing processing in the energy control device based on an operational input in the operational button according to a second modification.

In a second modification, the energy control device 3 performs the processing shown in FIG. 11 on the basis of the operational input in the operational button 13. In the present modification as well as in the first modification, when the acoustic impedance Z(t) at the time t is less than or equal to the minimum impedance value Zmin in step S104 (step S104—No), the controller 25 (the switch detector 52) updates the acoustic impedance Z(t) at the time t as the minimum impedance value Zmin (step S105), and holds the count time T at zero or resets the count time T to zero (step S111). After the processing in step S111 is performed, the processing returns to step S104.

When the acoustic impedance Z(t) at the time t is higher than the minimum impedance value Zmin in step S104 (step S104—Yes), the controller 25 (the judgment section 53) starts or continues the counting of the count time T as in the first modification (step S112). The count time T is not counted in a state where the processing in steps S104, S105, and S111 is repeated with time. However, in the present modification, the processing (judgment) in step S106 performed in the first modification is not performed. Thus, after the processing in step S112 is performed, the controller 25 (the judgment section 53) judges whether or not the count time T is equal to or more than the predetermined set time Tth (step S113). That is, whether or not the predetermined set time Tth has elapsed since the switch of the acoustic impedance Z to the gradually increasing state is judged.

When the count time T at the time t is less than the predetermined set time Tth (step S113—No), the processing returns to step S104. The controller 25 then again makes a judgment in step S104 after the time of the judgment target for step S113. In contrast, when the count time T at the time t is equal to or more than the predetermined set time Tth (step S113—Yes), the controller 25 stops the output of the ultrasonic electric energy (US) from the energy source 26 (the ultrasonic electric energy source 35) (step S107). In the present modification as well, after the output of the ultrasonic electric energy is stopped, the output of the high-frequency electric energy (HF) is stopped on the basis of the fact that the high-frequency impedance Z'(t) has become equal to or more than the threshold Z'th.

In the present modification, the energy control device 3 performs the processing shown in FIG. 11 on the basis of the operational input in the operational button 13. Thus, when the acoustic impedance Z changes as indicated by the solid line in FIG. 6, the controller 25 (the switch detector 52) sets the acoustic impedance Z(t1) at the time t1 as the minimum impedance value Zmin, and detects that the acoustic impedance Z has switched from the gradually decreasing state to the gradually increasing state at the time t1, as in the embodiment and others described above. In this instance, in the present modification, the controller 25 (the judgment section 53) sets the predetermined set time Tth1. The count time T in which the time t1 that is the switch time of the acoustic impedance Z to the gradually increasing state is zero is counted by the processing in step S112. After the time t1, the processing in steps S104 and S112, and the processing in step S113 using the predetermined set time Tth1 are repeated with time.

The controller 25 (the judgment section 53) judges by the processing in steps S104 and S113 that the acoustic impedance Z is continuously kept at a value higher than the minimum impedance value Zmin (the impedance value Z(t1)) before the predetermined set time Tth1 elapses from the time t1 (between the time t1 and the time t13). By the processing in step S107, the controller 25 stops the output of the ultrasonic electric energy (US) from the energy source 26 or immediately after the time t13.

When the acoustic impedance Z changes as shown in FIG. 8, the controller 25 (the switch detector 52) sets the acoustic impedance Z(t8) at the time t8 as the minimum impedance value Zmin, and detects that the acoustic impedance Z has switched from the gradually decreasing state to the gradually increasing state at the time t8, as in the embodiment and others described above. In this instance, in the present modification, the controller 25 (the judgment section 53) sets the predetermined set time Tth2. The count time T in which the time t8 that is the switch time of the acoustic impedance Z to the gradually increasing state is zero is counted by the processing in step S112. After the time t8, the processing in steps S104 and S112, and the processing in step S113 using the predetermined set time Tth2 are repeated with time.

When the acoustic impedance Z changes as shown in FIG. 8, the controller 25 judges that the acoustic impedance Z(t9) has become less than or equal to the acoustic impedance Z(t8) set as the minimum impedance value Zmin before the time t14 that is the time at which the predetermined set time Tth2 elapses from the time t8, at which the acoustic impedance Z switches to the gradually increasing state, by the repetition of the processing in steps S104, S112, S106, and S113. The acoustic impedance Z(t9) at the time t9 is updated as the minimum impedance value Zmin by the processing in S105, and the count time T is reset to zero by the processing in S111. The controller 25 (the switch detector 52) then updates acoustic impedance Z(t10) at the time t10 as the minimum impedance value Zmin, and detects that the acoustic impedance Z has switched from the gradually decreasing state to the gradually increasing state at the time t10. In this instance, the controller 25 (the judgment section 53) sets the predetermined set time Tth3. The count time T in which time t10 that is the switch time of the acoustic impedance Z to the gradually increasing state is zero is counted by the processing in step S112. After the time t10, the processing in steps S104 and S112, and the processing step S113 using the predetermined set time Tth3 are repeated with time.

The controller 25 (the judgment section 53) judges by the processing in steps S104 and S113 that the acoustic impedance Z is continuously kept at a value higher than the minimum impedance value Zmin (the impedance value Z(t10)) before the predetermined set time Tth3 elapses from the time t10 (between the time t10 and the time t15). By the processing in step S107, the controller 25 stops the output of the ultrasonic electric energy (US) from the energy source 26 at or immediately after the time t15.

When the acoustic impedance Z changes as shown in FIG. 10, the controller 25 (the switch detector 52) sets the acoustic impedance Z(t16) at the time t16 as the minimum impedance value Zmin, and detects that acoustic impedance Z has switched from the gradually decreasing state to the gradually increasing state at the time t16. In this instance, the controller 25 (the judgment section 53) sets the predetermined set time Tth4. The count. time T in which the time t16 that is the switch time of the acoustic impedance Z to the gradually increasing state is zero is counted by the processing in step S112. After the time t16, the processing in steps S104 and S112, and the processing in step S113 using the predetermined set time Tth4 are repeated with time.

The controller 25 (the judgment section 53) judges by the processing in steps S104 and S113 that the acoustic impedance Z is continuously kept at a value higher than the minimum impedance value Zmin (the impedance value Z(t16)) before the predetermined set time Tth4 elapses from the time t16 (between the time t16 and the time t17). By the processing in step S107, the controller 25 stops the output of the ultrasonic electric energy (US) from the energy source 26 at the time t17 or at the time t18 immediately after the time t17.

In the present modification as well, functions and advantageous effects similar to those in the embodiment and others described above are provided.

In the embodiment and others described above, the energy treatment device (1) includes the energy source (26) configured to output ultrasonic electric energy and high-frequency electric energy, the vibration generator (40) which is supplied with the ultrasonic electric energy from the energy source (26) and thereby generates ultrasonic vibration, and the end effector (20) configured to conduct a treatment by use of the ultrasonic vibration generated in the vibration generator (40) and the high-frequency electric energy supplied from the energy source (26). The impedance detector (51) detects the acoustic impedance (Z) with time in a state where the ultrasonic electric energy is output from the energy source (26), and the impedance detector (51) detects the high-frequency impedance (Z') with time in a state where the high-frequency electric energy is output from the energy source (26). The switch detector (52) detects a switch from the gradually decreasing state where the acoustic impedance (Z) gradually decreases with time to the gradually increasing state where the acoustic impedance (Z) gradually increases with time, on the basis of the detection result of the acoustic impedance (Z) in the impedance detector (51). The controller (25) controls the output state of the ultrasonic electric energy and the output state of the high-frequency electric energy from the energy source (26). In a state where the ultrasonic electric energy and the high-frequency electric energy are simultaneously output from the energy source (26), the controller (25) stops the output of the ultrasonic electric energy on the basis of at least the fact that the switch of the acoustic impedance (Z) from the gradually decreasing state to the gradually increasing state is detected by the switch detector (52), and the controller (25) stops the output of the high-frequency electric energy on the basis of the fact that the high-frequency impedance (Z') detected by the impedance detector (51) reaches the set threshold (Z'th).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An energy treatment device comprising:
   an energy source which can output ultrasonic electric energy and high-frequency electric energy;
   a vibration generator which is supplied with the ultrasonic electric energy from the energy source, and thereby which is configured to generate ultrasonic vibration;
   an end effector configured to conduct a treatment by use of the ultrasonic vibration generated in the vibration generator and the high-frequency electric energy supplied from the energy source;
   an impedance detector which is configured to detect acoustic impedance with time in a state where the ultrasonic electric energy is output from the energy source, and which is configured to detect high-frequency impedance with time in a state where the high-frequency electric energy is output from the energy source;
   a switch detector which is configured to detect a switch from a gradually decreasing state where the acoustic impedance gradually decreases with time to a gradually increasing state where the acoustic impedance gradually increases with time, on a basis of a detection result of the acoustic impedance in the impedance detector; and
   a controller which is configured to control the output state of the ultrasonic electric energy and the output state of the high-frequency electric energy from the energy source, wherein in a state where the ultrasonic electric energy and the high-frequency electric energy are simultaneously output from the energy source, the controller is configured to stop the output of the ultrasonic electric energy on a basis that a value which is a result of the subtraction of an impedance value at a time of the switch to the gradually increasing state from the acoustic impedance is equal to or more than a reference difference value or that the acoustic impedance is kept at a value higher than the impedance value at the time of the switch to the gradually increasing state before a predetermined set time elapses from the time of the switch to the gradually increasing state, after the switch of the acoustic impedance from the gradually decreasing state to the gradually increasing state is detected by the switch detector, and the controller is configured to stop the output of the high-frequency electric energy on a basis that the high-frequency impedance detected by the impedance detector reaches a set threshold.

2. The energy treatment device according to claim 1, wherein in the state where the ultrasonic electric energy and the high-frequency electric energy are simultaneously output from the energy source, the controller is configured to stop the output of the ultrasonic electric energy at and after the switch to the gradually increasing state and while the acoustic impedance is in the gradually increasing state.

3. The energy treatment device according to claim 1, wherein
the switch detector is configured to set, as a minimum impedance value, a first impedance value which is the acoustic impedance at the time of the switch to the gradually increasing state,
when detecting that the acoustic impedance reaches a second impedance value less than or equal to the first impedance value set as the minimum impedance value at and after the switch to the gradually increasing state, the switch detector is configured to update the minimum impedance value to the second impedance value, and
in the state where the ultrasonic electric energy and the high-frequency electric energy are simultaneously output from the energy source, the controller is configured to judge whether or not to stop the output of the ultrasonic electric energy on the basis of a change of the acoustic impedance with time from the second impedance value updated as the minimum impedance value at and after a time when the acoustic impedance reaches the second impedance value.

4. An energy control device which controls the supply of energy to an energy treatment instrument, the energy treatment instrument including an end effector configured to conduct a treatment by use of ultrasonic vibration and high-frequency electric energy, and a vibration generator which is supplied with ultrasonic electric energy and thereby configured to generate the ultrasonic vibration to be transmitted to the end effector, the energy control device comprising:
an energy source which can output the ultrasonic electric energy to be supplied to the vibration generator and the high-frequency electric energy to be supplied to the end effector;
an impedance detector which is configured to detect acoustic impedance with time in a state where the ultrasonic electric energy is output from the energy source, and which is configured to detect high-frequency impedance with time in a state where the high-frequency electric energy is output from the energy source;
a switch detector which is configured to detect a switch from a gradually decreasing state where the acoustic impedance gradually decreases with time to a gradually increasing state where the acoustic impedance gradually increases with time, on a basis of a detection result of the acoustic impedance in the impedance detector; and
a controller which is configured to control the output state of the ultrasonic electric energy and the output state of the high-frequency electric energy from the energy source, wherein in a state where the ultrasonic electric energy and the high-frequency electric energy are simultaneously output from the energy source, the controller is configured to stop the output of the ultrasonic electric energy on a basis that a value which is a result of the subtraction of an impedance value at a time of the switch to the gradually increasing state from the acoustic impedance is equal to or more than a reference difference value or that the acoustic impedance is kept at a value higher than the impedance value at the time of the switch to the gradually increasing state before a predetermined set time elapses from the time of the switch to the gradually increasing state, after the switch of the acoustic impedance from the gradually decreasing state to the gradually increasing state is detected by the switch detector, and the controller is configured to stop the output of the high-frequency electric energy on a basis that the high-frequency impedance detected by the impedance detector reaches a set threshold.

* * * * *